(12) United States Patent
Aziz et al.

(10) Patent No.: US 7,291,404 B2
(45) Date of Patent: Nov. 6, 2007

(54) ORGANIC LIGHT EMITTING DEVICES

(75) Inventors: Hany Aziz, Oakville (CA); George Vamvounis, Burnaby (CA); Nan-Xing Hu, Oakville (CA); Zoran D. Popovic, Mississauga (CA); Jennifer A. Coggan, Cambridge (CA)

(73) Assignee: LG.Philips LCD Co., Ltd., Seoul (KR)

( * ) Notice: Subject to any disclaimer, the term of this patent is extended or adjusted under 35 U.S.C. 154(b) by 246 days.

(21) Appl. No.: 10/702,859

(22) Filed: Nov. 6, 2003

(65) Prior Publication Data

US 2004/0209117 A1    Oct. 21, 2004

Related U.S. Application Data

(60) Provisional application No. 60/463,312, filed on Apr. 17, 2003.

(51) Int. Cl.
*H01J 1/62*      (2006.01)
*C09K 11/06*   (2006.01)

(52) U.S. Cl. .................. 428/690; 428/917; 313/504; 313/506; 257/40

(58) Field of Classification Search ............ 428/690, 428/917; 257/40; 313/504, 506; 546/62, 546/64; 548/149, 218, 223, 301.7, 420, 421; 136/263
See application file for complete search history.

(56) References Cited

U.S. PATENT DOCUMENTS

| | | | |
|---|---|---|---|
| 3,530,325 A | 9/1970 | Mehl et al. | 313/108 |
| 4,539,507 A | 9/1985 | VanSlyke et al. | 313/504 |
| 4,720,432 A | 1/1988 | VanSlyke et al. | 428/457 |
| 4,769,292 A | 9/1988 | Tang et al. | 428/690 |
| 4,770,976 A * | 9/1988 | Loerzer et al. | 430/281.1 |
| 6,392,339 B1 | 5/2002 | Aziz et al. | 313/504 |

FOREIGN PATENT DOCUMENTS

| | | | |
|---|---|---|---|
| JP | 2001-118683 | * | 4/2001 |
| JP | 2002-050473 | * | 2/2002 |

OTHER PUBLICATIONS

Neunhoeffer et al., Chemiluminescence of lophine and analogous compounds, Anorganische Chemie, Organische Chemie, Biochemie, Biophysik, Biologie, 21(6), 536-9, 1966.*
Guan et al., Bright red light-emitting electroluminescence devices based on a functionalized europium complex, New Journal of Chemistry, 2003, 27, 1731-1734.*
Yuji Hamada et al., "Influence of the Emission Site on the Running Durability of Organic Electroluminescent Devices", *Japanese Journal of Applied Physics*, vol. 34, Part 2, No. 7A, Jul. 1995, pp. L824-L826.
Ralf Fink et al., "Aromatic Polyethers With 1,3,5-Triazine Units as Hole Block/Electron Transport Materials in LEDs", *Macromolecular Symposia*, vol. 125, 1997, pp. 151-155.

* cited by examiner

*Primary Examiner*—Rena Dye
*Assistant Examiner*—Camie S. Thompson
(74) *Attorney, Agent, or Firm*—McKenna Long & Aldridge LLP (57) ABSTRACT

The present invention is an organic light emitting device (OLED) comprising an anode, a cathode and a luminescent region provided between the anode and the cathode. The luminescent region comprises an electron injection and transporting zone and at least one of a hole injection and transporting zone and a mixed charge transport layer. One or both of the electron injection and transporting zone and the mixed charge transporting layer comprises an azole compound represented by formula I and/or II. The provision of the novel azole compounds of the invention as electron transport materials within an organic electroluminescent device advantageously reduces power consumption and increases power conversion efficiency within the device and as such, are suitable for a variety of display applications.

62 Claims, 5 Drawing Sheets

ORGANIC LIGHT EMITTING DEVICES

CROSS-REFERENCE TO RELATED APPLICATIONS

This application claims the benefit of U.S. Provisional Application No. 60/463,312, filed Apr. 17, 2003, the disclosure of which is totally incorporated herein by reference.

BACKGROUND OF THE INVENTION

Organic light emitting devices (OLEDs) are useful for display applications and in particular, mobile hand held display applications. To achieve efficient electroluminescence OLEDs have typically been manufactured to include separate layers of a hole transport material (HTM) and an emitting electron transport material (ETM). During operation, an applied electric field causes positive charges (holes) and negative charges (electrons) to be respectively injected from the anode and the cathode of the OLED to recombine and thus produce light emission. In other known OLED displays, the hole transport and electron transport layers are doped with organic dyes in order to enhance the efficiency or to improve the stability of the OLED. OLEDs have also been developed in which hole transport material and emitting electron transport material are mixed together in one single layer. However, such single mixed layer organic light emiting devices are generally less efficient an unstable compared to multilayer organic light emitting devices. There have also been attempts to obtain electroluminescence from organic light emitting devices by introducing hole transport material and emitting electron transport material as dopants in an inert host material. However, such known devices have been found to be generally less efficient than conventional devices including separate layers of hole transport material and emitting electron transport material.

To date, organic light emitting devices as described above have relatively short operational lifetimes before their luminance drops to some percentage of its initial value. Methods of providing interface layers and doping have been developed to increase the operational lifetime of organic light emitting devices to several tens of thousands of hours for room temperature operation, however, the effectiveness of the known organic light emitting devices deteriorates dramatically for high temperature device operation, as the existing methods used to extend the device lifetimes lose their effectiveness at higher temperatures.

A simple organic electroluminescent (EL) device may comprise of a layer of an organic luminescent material conductively sandwiched between an anode, typically comprised of a transparent conductor, such as indium tin oxide, and a cathode, typically a low work function metal such as magnesium, calcium, aluminum, or the alloys thereof with other metals. The EL device functions on the principle that under an electric field, positive charges (holes) and negative charges (electrons) are respectively injected from the anode and cathode into the luminescent layer and undergo recombination to form excitonic states which subsequently emit light. A number of prior art organic electroluminescent devices have been prepared from a laminate of an organic luminescent material and electrodes of opposite polarity, which devices include a single crystal material, such as a single crystal anthracene, as the luminescent substance as described, for example, in U.S. Pat. No. 3,530,325. However, these devices usually require excessive excitation voltages on the order of 100 volts or greater.

An organic EL device can also be formed as a dual layer structure comprising one organic layer adjacent to the anode supporting hole transport, and another organic layer adjacent to the cathode supporting electron transport and acting as the organic luminescent zone of the device. Another alternate device configuration is comprised of three separate layers, a hole transport layer, a luminescent layer, and an electron transport layer, which layers are laminated in sequence and are sandwiched between an anode and a cathode. Optionally, a fluorescent dopant material can be added to the emission zone or layer whereby the recombination of charges results in the excitation of the fluorescent.

U.S. Pat. No. 4,539,507 discloses an EL device formed of a conductive glass transparent anode, a hole transporting layer of 1,1-bis(4-p tolylaminophenyl)cyclohexane, an electron transporting layer of 4,4'-bis(5,7-di-tert-pentyl-2-benzoxzolyl)stilben, and an indium cathode.

U.S. Pat. No. 4,720,432 discloses an organic EL device comprising a dual-layer hole injecting and transporting zone, one layer being comprised of porphyrinic compounds supporting hole injection and the other layer being comprised of aromatic tertiary amine compounds supporting hole transport.

U.S. Pat. No. 4,769,292 discloses an EL device employing a luminescent zone comprised of an organic host material capable of sustaining hole-electron recombination and a fluorescent dye material capable of emitting light in response to energy released by hole-electron recombination. A preferred disclosed host material is an aluminum complex of 8-hydroxyquinoline, namely tris(8-hydroxyquinolinate) aluminum.

U.S. Pat. No. 6,392,339 (the entirety of which is incorporated herein by reference) describes an OLED manufactured to provide operational stability at high temperature device operation conditions. The OLED comprises a mixed region or layer of a hole transport material and electron transport material having first and second surfaces, an electron transport material provided on one of the surfaces of the mixed region and an optional hole transport material on one of the other surfaces of the mixed region, where an anode is further provided in contact with the mixed region or the hole transport material and a cathode is provided in contact with the electron transport material or with a first surface of the mixed region.

Typically, the organic EL devices with multi-layered configurations comprise an electron transport layer in contact with a cathode. This electron transport layer is intended to assist injection of electrons from the cathode into the light-emitting layer. A variety of organic electron transport materials have been employed for this purpose. A class of such electron transport materials is comprised of the metal complexes of 8-hydroxyquinoline, as disclosed in U.S. Pat. Nos. 4,720,432. A another class of electron transport materials for EL devices is comprised of 1,3,5-oxidiazole compounds, such as those disclosed in *Japanese Journal of Applied Physics*, Part 2, vol. 34, L824 (1995). Also, certain 1,3,5-triazine containing materials have been reported as being a hole blocking layer in organic EL devices, see Fink et al. in *Macromolecular Symposia*, vol. 125, 151(1997).

While recent progress in organic EL research has elevated the potential of organic EL devices for widespread applications, the performance levels of current available devices may still be below expectations. Further, for visual display applications, organic luminescent materials should provide a satisfactory color in the visible spectrum, normally with emission maxima at about 460, 550 and 630 nanometers for blue, green and red. The aforementioned metal complexes of 8-hydroxyquinoline, such as tris(8-hydroxyquinolinate)aluminum, generally fluoresce in green or longer wavelength region. These electron transport materials may be suitable for use in EL devices with light emission in green or longer wavelength region, however, for blue-emitting EL devices they are of limited use. Although prior art electron transport materials may fluoresce in the blue region, the performance characteristics of the resulting EL devices still possess many disadvantages such as poor operation stability.

Thus, there continues to be a need for electron transport materials for organic EL devices, which are suitable for the design of EL devices with satisfactory emission in the visible spectrum of from blue to longer wavelength region. There is also a need for electron transport materials, which can improve EL device operation stability and durability, and a need for electron transport materials, which can enhance the EL charge transporting characteristics, thus lowering device driving voltages. Further, there is a need for electron transport materials, which are vacuum evaporable and form thin films with excellent thermal stability.

SUMMARY OF THE DISCLOSURE

This invention overcomes the above-described disadvantages of known organic light emitting devices (OLEDs) and provides improved organic light emitting devices having enhanced efficiency and operational lifetimes. In addition, the organic light emitting devices according to this invention provide operational stability with minimized power consumption and increased power conversion efficiency.

Accordingly, the organic light emitting devices according to this invention can be used for various applications, and especially technological applications that require minimized power consumption such as mobile hand held display devices. The invention provides for the use of certain azole compounds as an effective electron transport material and/or electron injecting material.

The organic light emitting devices according to this invention incorporate the use of novel azole compounds which leads to a lower driving voltage of the OLED and a higher power conversion efficiency.

According to an aspect of an object of the present invention, there is provided an organic electroluminescent (EL) device comprising an anode and a cathode, and an organic luminescent region containing an electron injection and transporting zone that comprises an azole compound or comprised of an azole electron acceptor.

According to another object of an aspect of the present invention there is provided an organic EL device comprising a supporting substrate, an anode, a hole injection and transporting zone, an electron injection and transporting zone, and in contact therewith a metal cathode, wherein the electron injection and transporting zone comprises a novel azole compound as the electron transport material. In aspects, the substrate is formed of glass and a buffer layer may additionally be provided on the anode. The device may further comprise a mixed charge transport layer of a luminescent material or of a mixture of a hole transport material and an electron transport material. To the mixture of hole transport and electron transport materials may be further added a luminescent material. Furthermore, a luminescent material may also be added to the electron injection and transporting zone and/or the hole injection and transporting zone. As such, a luminescent material may be incorporated anywhere within the luminescent region as desired as is understood by one of skill in the art.

According to another object of an aspect of the present invention there is provided an organic EL device comprising a supporting substrate, an anode, a hole injection and transporting zone, a mixed charge transport layer, an electron injection and transporting zone, and in contact therewith a metal cathode, wherein the electron injection transporting zone comprises a novel azole compound as the electron transport material. In aspects, the substrate is formed of glass and a buffer layer may additionally be provided on the anode.

According to yet another object of an aspect of the present invention there is provided an organic EL device comprising a supporting substrate, an anode, a hole injection and transporting zone, a mixed charge transport layer comprising a hole transport material and an electron transport material, and in contact therewith a metal cathode, wherein the mixed charge transport layer and/or the electron injection and transporting zone comprises an azole compound of the present invention. In aspects, the substrate is formed of glass and a buffer layer may additionally be provided on the anode. In other aspects, the hole injection and transporting zone is optional and the mixed charge transport layer may be of a luminescent material.

According to an aspect of the present invention is an electroluminescent device comprising an anode, a cathode and a luminescent region provided between said anode and cathode, said luminescent region comprising;

an electron injection and transporting zone and at least one of a hole injection and transporting zone and a mixed charge transport layer, wherein said electron injection and transporting zone and/or said mixed charge transporting layer comprises an azole compound of the formula:

(I)

wherein X represents CH or N;

Y is an atom or a group selected from the group consisting of O, S, and —N(R)—, wherein R is a hydrocarbyl group of from 1 to about 30 carbons;

$R^1$ and $R^2$ are each a substituent selected from the group consisting of hydrogen, an alkyl group of from 1 to about 25 carbon atoms, an aryl group of about 6 to about 30 carbon atoms, an alkoxy group of from 1 to about 25 carbon atoms, a halogen, and a cyano group; and Ar is an aromatic component.

Preferred azole compounds are represented by the formula:

(II)

wherein $R^1$, $R^2$, $R^3$ and $R^4$ are each a substituent, which may be selected from the group consisting of hydrogen, an alkyl group with for example from 1 to about 25 carbon atoms and more specifically about 1 to about 6 carbon atoms, an aryl group with about 6 to about 30 carbon atoms, an alkoxy group with from 1 to about 25 carbon atoms and more specifically from 1 to about 6 carbon atoms, a halogen, a cyano group and the like;

$R^5$ is a substituent which may be selected from the group consisting of hydrogen, an alkyl group with for example from 1 to about 25 carbon atoms and more specifically about 1 to about 6 carbon atoms, an aryl group with about 6 to about 30 carbon atoms, an alkoxy group with from 1 to about 25 carbon atoms and more specifically 1 to about 6 carbon atoms, a halogen, a cyano group and the like; and wherein R is a hydrocarbyl group of from 1 to about 30 carbons, preferably R is an alkyl group having from 1 to about 15 carbon atoms, or an aryl group containing about 6 to about 20 carbon atoms.

According to another aspect of the present invention is an electroluminescent device comprising an anode, a cathode and a luminescent region provided between said anode and cathode, said luminescent region comprising;

an electron injection and transporting zone and at least one of a hole injection and transporting zone and a mixed charge transport layer, wherein said electron injection and transporting zone and/or said mixed charge transporting layer comprises an azole compound of the formula:

(II)

wherein $R^1$, $R^2$, $R^3$, $R^4$ and $R^5$ are each a substituent selected from the group consisting of hydrogen, an alkyl group of from 1 to about 25 carbon atoms, an aryl group of about 6 to about 30 carbon atoms, an alkoxy group with from 1 to about 25 carbon atoms, a halogen, and a cyano group; and R is a hydrocarbyl group of from 1 to about 30 carbons or an aryl group containing about 6 to about 20 carbons.

According to yet another aspect of the present invention is an organic electroluminescent device comprising;
an anode and a cathode;
a luminescent region provided between said anode and cathode, said luminescent region comprising:
an electron injection and transporting zone adjacent said cathode and a hole injection and transporting zone adjacent said anode, wherein said electron injection and transporting zone comprises one or more azole compounds of formula I and/or formula II.

The azole compounds of the present invention can readily be evaporated to deposit as thin films with desirable morphological and thermal stability and exhibit acceptable to excellent electron transport properties, chemical and electrical stability. It is understood that the invention encompasses the use of one or a mixture of the azole compounds of the invention. In other embodiments, the azole compounds of the invention may be used with one or more conventional electron transport materials.

According to another object of an aspect of the present invention, is a method to reduce power consumption and increase power conversion efficiency in an organic light emitting device comprising an anode, a cathode and a luminescent region provided between said anode and cathode, said luminescent region comprising;
an electron injection and transporting zone and at least one of a hole injection and transporting zone and a mixed charge transport layer,
wherein said method comprises providing an azole compound of the formula I and/or II in said electron injection and transporting zone and/or said mixed charge transporting layer.

According to still another aspect of the present invention is an electron transport material provided as an electron transport layer in an electroluminescent device, the electron transport material comprising an azole compound selected from the group consisting of an azole compound of formula I and/or formula II as described herein. In aspects the electron transport material of the invention can be used in a variety of applications including but not limited to photoreceptors, solar cells and/or organic electronics as is understood by one of skill in the art. Thus in accordance with the invention are photoreceptors, solar cells and/or organic electronics comprising the electron transport material of formula I and/or II.

In embodiments of the invention wherein an azole compound of formulas (I) and/or (II) are selected as an electron transport material, the organic EL devices of the present invention can provide a number of improved performance characteristics. Such improved performance characteristics include but are not limited to high luminance, low driving voltages, long device operation stability and extended useful durability, the enablement of light emission from about 400 nanometers to about 700 nanometers and the use of a cathode comprised of a metal such as aluminum.

BRIEF DESCRIPTION OF THE DRAWINGS

Embodiments of this invention will be described in detail, with reference to the following figures, in which:

FIGS. 2A-2C illustrate three different configurations of OLEDs.

DETAILED DESCRIPTION

The present invention provides improved organic electroluminescent devices having enhanced efficiency and operational lifetimes. Furthermore, the electroluminescent devices according to the invention provide operational stability with minimized power consumption and increased power conversion efficiency. These and other advantages are effected by the use of novel electron transport materials as the electron transport component, i.e. the electron transport and/or electron injecting material, in an electroluminescent device. As provided adjacent a cathode layer within an electroluminescent device, the use of the novel azole compounds of the invention as electron transport materials function for both electron transport as well as electron injection.

The electron transport component for use in the organic EL devices of the present invention comprise azole compounds represented by the formula (I).

(I)

wherein, X represents CH or N;

Y is an atom or a group, which can be selected from the group consisting of O, S, and —N(R)—, wherein R is a hydrocarbyl group of from 1 to about 30 carbons, preferably R is an alkyl group having from 1 to about 15 carbons, or an aryl group containing about 6 to about 20 carbons. Illustrative examples of alkyl for R include a methyl, an ethyl, a propyl, a butyl and the like; examples of the aryl group for R include a phenyl, a naphthyl and the like;

$R^1$ and $R^2$ are each a substituent selected from the group consisting of hydrogen, an alkyl group with for example from 1 to about 25 and more specifically from 1 to about 6 carbon atoms, an aryl group with about 6 to about 30 carbon atoms, an alkoxy group with from 1 to about 25 and more specifically from 1 to about 6 carbon atoms, a halogen, a cyano group and the like. Preferable examples of $R^1$ and $R^2$ include a methyl, a butyl, a fluorine atom and the like;

Ar is an aromatic component, such as an aryl group having, for example, from about 6 to about 30 carbons. Illustrative examples of aryl group for Ar can be selected from the group consisting of a phenyl, a naphthyl, an anthryl and the like. The aromatic component for Ar may be a heteroaryl group of for example, a pyridyl, and a quinolyl, and the like.

Preferred azole compounds of the invention are illustrated by the following:

(II)

wherein $R^1$, $R^2$, $R^3$ and $R^4$ are each a substituent, which may be selected from the group consisting of hydrogen, an alkyl group with for example from 1 to about 25 carbon atoms and more specifically from 1 to about 6 carbon atoms, an aryl group with about 6 to about 30 carbon atoms, an alkoxy group with from 1 to about 25 carbon atoms and more specifically from 1 to about 6 carbon atoms, a halogen, a cyano group and the like. Preferable examples of alkyl group for $R^2$, $R^3$ and $R^4$ include a methyl, a butyl and the like.

$R^5$ is a substituent selected from the group consisting of hydrogen, an alkyl group with for example from 1 to about 25 carbon atoms and more specifically from 1 to about 6 carbon atoms, an aryl group with about 6 to about 30 carbon atoms, an alkoxy group with from 1 to about 25 carbon atoms and more specifically from 1 to about 6 carbon atoms, a halogen, a cyano group and the like. Illustrative examples of alkyl group for $R^5$ include a methyl, a butyl and the like, and preferably a tertiary butyl. Specific examples of aryl group for $R^5$ include a phenyl, a naphthyl, a styryl and the like, and preferably a 2-naphthyl group. R is a hydrocarbyl group of from 1 to about 30 carbons. Preferably R is an alkyl group having from 1 to about 15 carbon atoms, or an aryl group containing about 6 to about 20 carbon atoms. Illustrative examples of alkyl for R include a methyl, an ethyl, a propyl, a butyl and the like. Illustrative examples of aryl group for R include a phenyl, a naphthyl and the like.

The azole compound electron transport materials of the invention and herein described can be prepared by standard synthetic processes. The compounds thus obtained may be confirmed by elemental analysis, NMR or IR spectrometric indentification techniques as is understood by one of skill in the art. Illustrative example of the synthesis of various azole compounds of the invention are provided in the examples.

Specific examples of azole compounds of Formula (I) and (II) include but are not limited to 1-methyl-2-(phenyl) imidazo[4,5-f]-[1,10] phenanthroline, 1-methyl-2-(2-pyridyl)imidazo[4,5-f]-[1,10] phenanthroline, 1-methyl-2-(1naphthyl)imidazo [4,5-f]-[1,10] phenanthroline, 1-methyl-2-(9-anthryl)imidazo [4,5-f]-[1,10] phenanthroline, 1-methyl-2-(9-anthryl-10-methyl)imidazo[4,5-f]-[1,

10] phenanthroline, 1-methyl -2-(9-anthryl-10-t-butyl)imidazo[4,5-f]-[1.01] phenanthroline, 1-methyl-2-(9-anthryl-10-naphthyl)imidazo [4,5-f]-[1,10] phenanthroline (II-1 to II-7) and the like.

Structural formulas II-1 through II-7 are depicted below.

II-1: 1-methyl-2-(phenyl)imidazo[4,5-f]-[1,10]phenanthroline

II-2: 1-methyl-2-(2-pyridyl)imidazo[4,5-f]-[1,10]phenanthroline

II-3: 1-methyl-2-(1-naphthyl)imidazo[4,5-f]-[1,10]phenanthroline

II-4: 1-methyl-2-(9-anthryl)imidazo[4,5-f]-[1,10]phenanthroline

II-5: 1-methyl-2-(9-anthryl-10-methyl)imidazo[4,5-f]-[1,10]phenanthroline -continued
II-6: 1-methyl-2-(9-anthryl-10-t-butyl)imidazo[4,5-f]-[1,10]phenanthroline II-7: 1-methyl-2-(9-anthryl-10-naphthyl)imidazo[4,5-f]-[1,10] phenanthroline The azole compounds of the invention are electron transport materials that may be formed as thin films with excellent thermal stability by vacuum evaporation.

In embodiments, the present invention relates to organic electroluminescent (EL) devices comprising an anode, a luminescent region, and a cathode, wherein the luminescent region comprises at least one zone and/or layer containing one or more azole compounds of Formulas I and/or II. In a preferred embodiment, the azole compound is of formula (II).

Figure 1:
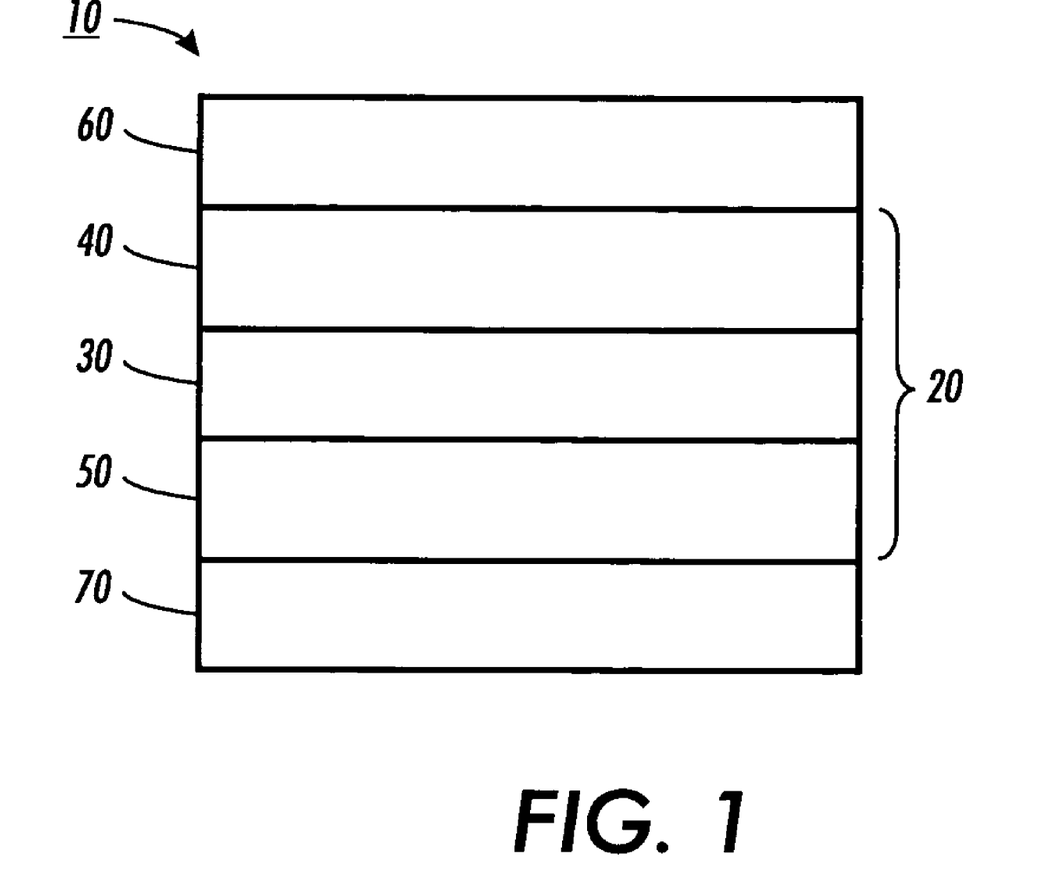
FIG. 1 illustrates a schematic of an OLED according to one embodiment of the present invention, having an electron injection and transporting zone, a mixed charge transport layer and a hole injection and transporting region.

An exemplary embodiment of an organic light emitting device (OLED) according to this invention is shown in FIG. 1. The organic light emitting device 10 has a luminescent region 20 that comprises a mixed charge transport layer 30, an electron injection and transporting zone 40 and an optional hole injection and transporting zone 50. A cathode 60 is provided adjacent and in contact with the electron injection and transporting zone 40. An anode 70 is provided either directly adjacent and in contact with the mixed charged transport layer 30 or alternatively directly adjacent and in contact with the optional hole injection and transporting zone 50. While not illustrated in FIG. 1, the organic light emitting device is provided on a substrate, with the anode 70 being directly adjacent and on top in contact with the substrate. An optional protective layer may be provided on top and in contact with the cathode 60. The azole compounds of the invention may be provided within the electron injection and transporting zone 40 and/or in the mixed charge transport layer 30.

In an embodiment of the invention, the EL devices of the present invention comprises a supporting substrate of, for example, glass, an anode thereover of, for example, indium tin oxide in a thickness of from about 1 to about 500 nanometers and preferably from about 30 to about 100 nanometers (throughout the thickness ranges for each layer are examples and other suitable thickness may be selected), optionally a buffer layer in contact with the anode and comprised of a conductive component or hole transport materials in a thickness from about 5 to about 500 nanometers and preferably from about 10 to about 100 nanometers, an organic hole injecting and transporting zone thereover of, for example, an aromatic tertiary amine in a thickness of from about 1 to about 200 nanometers and preferably from about 5 to about 100 nanometers; an organic electron injection and transporting zone in contact with the hole injection and transporting zone comprised of the azole compounds of the formulas or encompassed by the formulas illustrated herein in a thickness of from about 5 to about 300 nanometers and preferably from about 10 to about 100 nanometers, and in contact therewith a low work function metal as a cathode. In this EL device embodiment, the hole injection and transporting zone or the electron injection and transporting zone may optionally further contain a luminescent material of, for example, from about 0.01 weight percent to about 10 weight percent of a fluorescent dye or from about 0.01 weight percent to about 25 weight percent of a phosphorescent dye.

In another embodiment of the invention, the EL devices of the present invention can be comprised of a supporting substrate of, for example, glass, an anode thereover of, for example, indium tin oxide in a thickness of from about 1 to about 500 nanometers and preferably from about 30 to about 100 nanometers (throughout the thickness ranges for each layer are examples and other suitable thickness may be selected), optionally a buffer layer in contact with the anode and comprised of a conductive component or hole transport materials in a thickness from about 5 to about 500 nanometers and preferably from about 10 to about 100 nanometers, an organic hole injection and transporting zone thereover of, for example, an aromatic tertiary amine in a thickness of from about 1 to about 200 nanometers and preferably from about 5 to about 100 nanometers; a mixed charge transport layer comprised of an organic luminescent material of, for example, a fluorescent or a phosphorescent material, in a thickness of from about 1 to about 200 nanometers and preferably from about 5 to about 100 nanometers, an organic electron injection and transporting zone in contact with the mixed charge transport layer comprised of the azole compounds of the formulas or encompassed by the formulas illustrated herein in a thickness of from about 5 to about 300 nanometers and preferably from about 10 to about 100 nanometers, and in contact therewith a low work function metal as a cathode. In this EL device, light emission may originate from the mixed charge transport layer, of which may optionally further contain a luminescent dopant material of, for example, from about 0.01 weight percent to about 10 weight percent of a fluorescent dye or from about 0.01 weight percent to about 25 weight percent of a phosphorescent dye.

In yet another embodiment of the invention, the EL devices of the present invention can be comprised of a supporting substrate of, for example, glass, an anode thereover of, for example, indium tin oxide in a thickness of from about 1 to about 500 nanometers and preferably from about 30 to about 100 nanometers (throughout the thickness ranges for each layer are examples and other suitable thickness may be selected), optionally a buffer layer in contact with the anode and comprised of a conductive component or hole transport materials in a thickness from about 5 to about 500 nanometers and preferably from about 10 to about 100 nanometers, an organic hole injection and transporting zone thereover of, for example, an aromatic tertiary amine in a thickness of from about 1 to about 200 nanometers and preferably from about 5 to about 100 nanometers; a mixed charge transport layer comprised of a hole transport material and an electron transport material in a thickness of from about 1 to about 200 nanometers and preferably from about 5 to about 100 nanometers, an organic electron injection and transporting zone in contact with the mixed charge transport layer comprised of the azole compounds encompassed by the formulas illustrated herein in a thickness of from about 5 to about 300 nanometers and preferably from about 10 to about 100 nanometers, and in contact therewith a low work function metal as a cathode. Typically, the mixed charge transport layer described herein comprises from about 20 weight percent to about 80 weight percent of the hole transport material, and from about 80 weight percent to about 20 weight percent of the electron transport material, preferably comprises, for example, from about 35 weight percent to about 65 weight percent of the hole transport material, and from about 65 weight percent to about 35 weight percent of the electron transport material. Suitable hole transport materials for forming the mixed layer include aromatic tertiary amines, indolocarbazoles, aromatic hydrocarbon compounds and mixtures thereof. The electron transport material of the mixed layer may comprise an azole compound encompassed by the formulas illustrated herein, or alternatively, the electron transport material may comprise known conventional electron transport materials such as metal chelates, stilbenes, triazines, aromatic hydrocarbons and the like and mixtures thereof. Furthermore, the mixed charge transport layer may further contain a luminescent material of, for example, from about 0.01 weight percent to about 10 weight percent of a fluorescent luminescent material or from about 0.01 weight percent to about 25 weight percent of a phosphorescent luminescent material, or other luminescent materials where all weight percentages are based on the total weight of materials comprising the mixed layer. With respect to this embodiment, the organic electron injection and transporting zone, alternatively, may comprise known conventional electron transport materials such as metal chelates, stilbenes, triazines, aromatic hydrocarbons and the like and mixtures thereof. The electron transport material of the mixed charge transport layer may comprise azole compounds encompassed by the formulas illustrated herein. So long as at least one of the electron injection and transporting zone adjacent the cathode or the electron transport material present in the mixed charge transport layer (or both) comprises an azole compound of the invention. In this embodiment, it is also possible to provide an azole compound of the present invention both within the electron injection and transporting zone as well as in the mixed charge transport layer. Furthermore, where the mixed charge transporting layer contains hole transport material, a further hole injection and transporting zone is optional within the luminescence region of the device.

It is understood by one of skill in the art that in each embodiment of the invention as described herein, the electron injection and transporting zone may comprise one or more layers where one or more of the layers may contain an azole compound of the invention. It is also understood that such layers may also incorporate one or more conventionally used electron transport materials such as for example $Alq_3$. Furthermore, the azole compounds of the invention may be incorporated in only a part or portion of any layer or layers of the electron injection and transporting zone.

All the organic layers described herein, the buffer layer, the hole transport layer, the light emitting layer, and the electron transport layer, can be formed by any suitable method, for example, by vacuum evaporation as is understood by one of skill in the art. The method can also be applied for forming any of the layers comprising more than one component. For example, the mixed layer can be formed by co-evaporating the hole transport material, the electron transport material, and the optional luminescent material.

The organic EL devices of the present invention comprise a supporting substrate. Illustrative examples of supporting substrates include polymeric components, glass and the like, and polyesters like MYLAR®, polycarbonates, polyacrylates, polymethacrylates, polysulfones, quartz, and the like. Other substrates can also be selected provided, for example, it can effectively support the other layers, and that it does not interfere with the device functional performance. The thickness of the substrate can be, for example, from about 25 to about 1,000 microns or more, and, for example, from about 50 to about 500 microns depending, for example on the structural demands of the device.

Examples of the anode which is contiguous to the substrate, include positive charge injecting electrodes such as indium tin oxide, tin oxide, gold, platinum, or other suitable materials such as electrically conductive carbon, it-conjugated polymers such as polyaniline, polypyrrole, and the like with, for example, a work function equal to, or greater than about 4 electron volts, and more specifically, from about 4 to about 6 electron volts. The thickness of the anode can range from about 1 to about 500 nanometers with the preferred range being dictated by the optical constants of the anode material. One preferred range of anode thickness is from about 30 to about 100 nanometers.

An alternative buffer layer may be provided adjacent the anode of an electroluminescent device of the invention. The buffer layer primarily functions to facilitate efficient injection of holes from the anode, and improves the adhesion between the anode and the organic hole injection and transporting zone, thus further improving the device operation stability. The buffer layer comprises conductive materials such as polyaniline and its acid-doped forms, polypyrrole, poly(phenylene vinylene), and known semiconductive organic materials; porphyrin derivatives disclosed in U.S. Pat. No. 4,356,429 (the disclosure of which is totally incorporated herein by reference), such as 1,10,15,20-tetraphenyl-21H,23H-porphyrin copper (II); copper phthalocyanine, copper tetramethyl phthalocyanine; zinc phthalocyanine; titanium oxide phthalocyanine; magnesium phthalocyanine; and the like.

Another class of hole transporting materials that can be selected for the buffer layer of the invention are the aromatic tertiary amines such as those disclosed in U.S. Pat. No. 4,539,507 (the disclosure of which is totally incorporated herein by reference). Representative examples of aromatic tertiary amines are bis(4-dimethylamino-2-methylphenyl) phenylmethane, N,N,N-tri(p-tolyl)amine, 1,1-bis(4-di-p-tolylaminophenyl)cyclohexane, 1,1-bis(4-di-p-tolylaminophenyl)-4-phenyl cyclohexane, N,N'-diphenyl-N,N'-bis(3-methylphenyl)-1,1'-biphenyl-4,4'-diamine, N,N'-diphenyl-N,N'-bis(3-methylphenyl)-1,1'-biphenyl-4,4'-diamine, N,N'-diphenyl-N,N'-bis(4-methoxyphenyl)-1,1'-biphenyl-4,4'-diamine, N,N,N',N'-tetra-p-tolyl-1,1'-biphenyl-4,4'-diamine, N,N'-di-1-naphthyl-N,N'-diphenyl-1,1'-biphenyl-4,4'-diamine, and the like. Another class of aromatic tertiary amines selected for the hole transporting layer is polynuclear aromatic amines, such as N,N-bis-[4'-(N-phenyl-N-m-tolylamino)-4-biphenylyl]aniline; N,N-bis-[4'-(N-phenyl-N-m-tolylamino)-4-biphenylyl]-m-toluidine; N,N-bis-[4'-(N-phenyl-N-m-tolylamino)-4-biphenylyl]-p-toluidine; N,N-bis-[4'-(N-phenyl-N-p-tolylamino)-4-biphenylyl]aniline; N,N-bis-[4'-(N-phenyl-N-p-tolylamino)-4-biphenylyl]-m-toluidine; N,N-bis-[4'-(N-phenyl-N-p-tolylamino)-4-biphenylyl]-p-toluidine; N,N-bis-[4'-(N-phenyl-N-p-chlorophenylamino)-4-biphenylyl]-m-toluidine; N,N-bis-[4'-(N-phenyl-N-m-chlorophenylamino)-4-biphenylyl]-m-toluidine; N,N-bis-[4'-(N-phenyl-N-m-chlorophenylamino)-4-biphenylyl]-p-toluidine; N,N-bis-[4'-(N-phenyl-N-m-tolylamino)-4-biphenylyl]-p-chloroaniline; N,N-bis-[4'-(N-phenyl-N-p-tolylamino)-4-biphenylyl]-m-chloroaniline; N,N-bis-[4'-(N-phenyl-N-m-tolylamino)-4-biphenylyl]-1-aminonaphthalene and the like.

The buffer layer may also be comprised of aromatic tertiary amines and may further include a stabilizer as disclosed in U.S. Pat. No. 5,846,666 (the disclosure of which is totally incorporated herein by reference), a stabilizer comprising certain hydrocarbon compounds such as rubrene, 4,8-diphenylanthrecene, and the like. The buffer layer can be prepared by forming one of the above compounds into thin film by known methods, such as vapor deposition or spin coating. The thickness of buffer layer thus formed is not particularly limited, and can be in a range of from about 5 nanometers to about 300 nanometers, and preferably from about 10 nanometers to about 100 nanometers.

The hole injection and transporting zone comprises a hole transporting material with a thickness ranging from about 1 nanometer to about 200 nanometers, and preferably from about 5 nanometers to about 100 nanometers. Any conventional suitable aromatic amine hole transporting material described for the buffer layer may also be selected for forming this layer.

A preferred class of hole transporting materials selected for forming the hole injection and transporting zone or for use as a hole transport material in the mixed charge transport layer are N,N,N',N'-tetraaryl benzidines, such as N,N'-diphenyl-N,N'-bis(4-methoxyphenyl)-1,1'-biphenyl-4,4'-diamine, N,N,N',N'-tetra-p-tolyl-1,1'-biphenyl-4,4'-diamine, N,N'-di-1-naphthyl-N,N'-diphenyl-1,1'-biphenyl-4,4'-diamine, and the like, and 4,4'-bis(9-carbazolyl)-1,1'-biphenyl compounds, such as 4,4'-bis(9-carbazolyl)-1,1'-biphenyl compounds include 4,4'-bis(9-carbazolyl)-1,1'-biphenyl and 4,4'-bis(3-methyl-9-carbazolyl)-1,1'-biphenyl, and the like.

Examples of luminescent materials suitable for use in the mixed charge transport layer include the metal chelates of 8-hydroxyquinoline as disclosed in U.S. Pat. Nos. 4,539, 507; 5,151,629, and 5,150,006 (the disclosures of which are totally incorporated herein by reference). Illustrative specific examples of luminescent materials or compounds include tris(8-hydroxyquinolinate)aluminum, a preferred one, tris(8-hydroxyquinolinate)gallium, bis(8-hydroxyquinolinate) magnesium, bis(8-hydroxyquinolinate)zinc, tris(5-methyl-8-hydroxyquinolinate)aluminum, tris(7-propyl-8-quinolinolato)aluminum, bis[benzo{f}-8-quinolinate]zinc, bis(10-hydroxybenzo[h]quinolinate) beryllium, and the like. Also, another preferred class of luminescent materials include butadienes, such as 1,4-diphenylbutadiene and tetraphenylbutadiene, and stilbenes, and the like as illustrated in U.S. Pat. Nos. 4,356,429 and 5,516,577 (the disclosures of which are totally incorporated herein by reference).

The fluorescent materials is present in, for example, from about 0.01 to about 10 weight percent, and preferably from about 1 to about 5 weight percent of the layer. Illustrative examples of fluorescent materials include dyes selected, for example, from the group consisting of coumarin, dicyanomethylene pyranes, polymethine, oxabenzanthrane, xanthene, pyrylium, carbostyl, perylene, and the like; a dye selected from the group consisting of quinacridone derivatives. Illustrative examples of quinacridone dyes include quinacridone, 2-methylquinacridone, 2,9-dimethylquinacridone, 2-chloroquinacridone, 2-fluoroquinacridone, 1,2-benzoquinacridone, N,N'-dimethylquinacridone, N,N'-dimethyl-2-methylquinacridone, N,N'-dimethyl-2,9-dimethylquinacridone, N,N'-dimethyl-2-chloroquinacridone, N,N'-dimethyl-2-fluoroquinacridone, N,N'-dimethyl-1,2-benzoquinacridone, and the like. A preferred class of fluorescent materials are fused ring fluorescent dyes, examples of which are perylene, rubrene, anthracene, coronene, phenanthrecene, pyrene and the like, as illustrated in U.S. Pat. No. 3,172,862 (the disclosure of which is totally incorporated herein by reference). Also, fluorescent materials that can be used as a dopant include butadienes, such as 1,4-diphenylbutadiene and tetraphenylbutadiene, and stilbenes, and the like as illustrated in U.S. Pat. Nos. 4,356,429 and 5,516,577 (the disclosures of which are totally incorporated herein by reference).

The phosphorescent dye can be selected from, for example, organometallic compounds containing a heavy metal atom that can result in strong spin-orbit coupling, such as disclosed in Baldo et. al., "Highly efficient organic phosphorescent emission from organic electroluminescent devices", *Letters to Nature*, Volume 395, pp 151-154 (1998). Preferred examples include 2,3,7,8,12,13,17,18-octaethyl-21H,23H-phorpine platinum(II) (PtOEP) and others, such as, for example, those disclosed in U.S. Pat. No. 6,048,630 (the disclosure of which is totally incorporated herein by reference), and fac tris(2-phenylpyridine)iridium (Ir(ppy)$_3$).

The cathode can be comprised of any suitable material such as a metal, including high, for example from about 4.0 eV to about 6.0 eV, or low work function component, such as metals with, for example, an eV of from about 2.5 eV to about 4.0 eV (electron volts). The cathode can be derived from a combination of a low work function metal (about 4 eV, for example from about 2 to about 4 eV) and at least one other metal. Effective proportions of the low work function metal to the second or one other metal are from less than about 0.1 percent to about 99.9 percent by weight. Illustrative examples of low work function metals include alkaline metals such as lithium or sodium, Group 2A or alkaline earth metals such as beryllium, magnesium, calcium, or barium, and Group III metals including rare earth metals and the actinide group metals such as scandium, yttrium, lanthanum, cerium, europium, terbium, or actinium. Lithium, magnesium and calcium are preferred low work function metals.

The thickness of cathode may range from, for example, about 10 nanometers to about 500 nanometers. The Mg:Ag cathodes of U.S. Pat. No. 4,885,211 (the disclosure of which is totally incorporated herein by reference), constitute one preferred cathode construction. Another preferred cathode described in U.S. Pat. No. 5,429,884 (the disclosure of which are totally incorporated herein by reference), wherein the cathodes are formed from lithium alloys with other high work function metals such as aluminum and indium.

Both the anode and the cathode of the EL devices of the present invention may contain a protective coating thereon as is understood by one of skill in the art. Furthermore, the anode and cathode can be of any convenient forms. A thin conductive layer can be coated onto a light transmissive substrate, for example a transparent or substantially transparent glass plate or plastic film. The EL device may include a light transmissive anode formed from tin oxide or indium tin oxide coated on a glass plate. Also, very thin, for example less than about 200 Å, and more specifically, from about 75 to about 150 Angstroms, light-transparent metallic anodes can be used, such as gold, palladium, and the like. In addition, transparent or semitransparent thin layers, for example from 50 to about 175 Angstroms of conductive carbon or conjugated polymers such as polyaniline, polypyrrole, and the like can be selected as anodes. Any light transmissive polymeric film can be employed as the substrate. Additional suitable forms of the anode and cathode are illustrated in U.S. Pat. No. 4,885,211 (the disclosure of which is totally incorporated herein by reference).

An optional protective layer provided over and in contact with the cathode can comprise any suitable metal such as silver, gold, or non-conductive materials such as silicone oxide and the like.

Figure 2A:
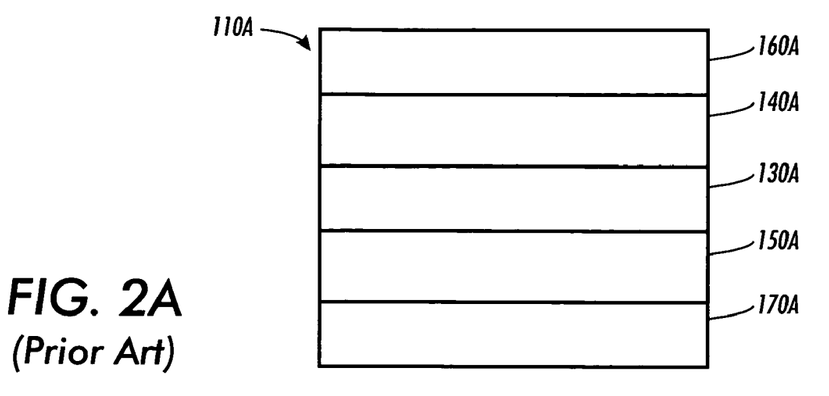
FIG. 2A is a conventional organic light emitting device.
Figure 2B:
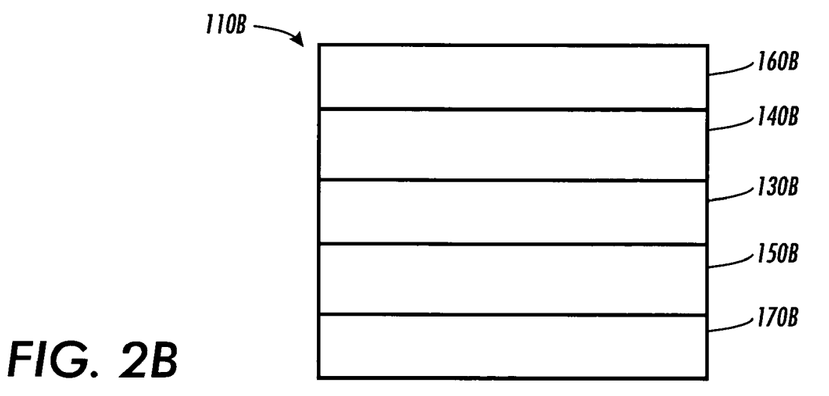
FIG. 2B is an organic light emitting device of the invention incorporating an arylimidazole derivative forming the entire electron injection and transporting zone.
Figure 2C:
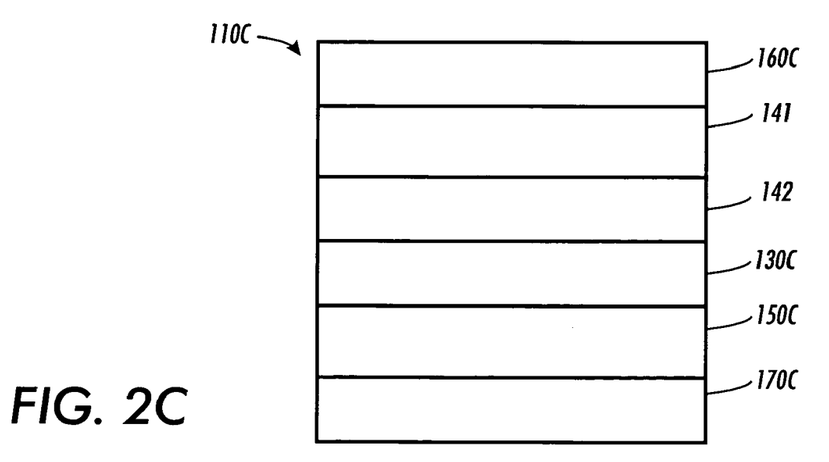
FIG. 2C is an organic light emitting device of the invention incorporating an arylimidazole derivative (MePA) forming only a portion of the electron injection and transporting zone.

A representative configuration of an OLED 110A of the prior art is illustrated in FIG. 2A where Alq3 is used as the electron transport material in the electron injection and transporting zone 140A. Representative configurations of the OLEDs (110B, 110C) of the present invention are illustrated in FIGS. 2B and 2C where MePa (1-methyl-2-(9-anthryl)imidazo[4,5-f]-[1,10]phenanroline) is incorporated in the electron injection and transporting zone 140B and the electron injection layer 141. All three OLED configurations were fabricated using conventional thermal deposition in vacuum procedures as commonly used for OLED fabrication as is understood by one of ordinary skill in the art. The term "Alq3" refers to a compound where either of the following chemical names for Alq3 is acceptable: tris(8-hydroxyquinolinate)aluminum or the IUPA nomenclature of tris(8-hydroxyquinolinato)aluminum). The term "NPB" refers to compound where either of the following chemical names is acceptable: N,N'-di-1-naphthyl-N,N'-diphenyl1,'1-biphenyl-4,4'-diamine, or N,N'-di-1-naphthyl-N,N'-diphenyl-benzidine.

FIG. 2A represents a conventional OLED configuration (a control or reference OLED) where the cathode 160A is formed from Mg:Ag alloy, the electron injection and transporting zone 140A is formed from Alq3 (200 Angstroms). The mixed charge transport layer 130A is of hole transport material and electron transport material. The hole injection and transporting zone 150A is formed of NPB (200 Angstroms) and the anode 170A is indium tin oxide (ITO). This conventional OLED configuration of FIG. 2A is represented as the control in FIGS. 3, 4 and 5.

FIG. 2B shows one embodiment of an OLED 110B of the present invention where the arylimidazole derivative MePA forms the entire electron injection and transporting zone 140B which has a thickness of 200 Angstroms. In this embodiment, the cathode 160B is formed from Mg:Ag alloy, the mixed charge transport layer 130B is of hole transport material and electron transport material. The hole injection and transporting zone 150B is formed of NPB (200 Angstroms) and the anode 170B is indium tin oxide (ITO).

FIG. 2C shows another embodiment of an OLED 110C of the present invention where the arylimidazole derivative MePA forms only a portion of the electron injection and transporting zone (i.e. the MePA forms one layer therein, the electron injection layer 141 (100 Angstroms) which is the layer adjacent to the cathode 160C). In this embodiment the MePA forms only a layer or portion of the electron injection and transporting zone that is directly adjacent the Mg:Ag alloy cathode. Alq3 forms another layer, the electron transport layer 142 (100 Angstroms), within the electron injection and transporting zone. Layers 141 and 142 together constitute the electron injection and transporting zone. The mixed charge transport layer 130C is of hole transport material and electron transport material. The hole injection and transporting zone 150C (200 Angstroms) is formed of NPB and the anode 170C is indium tin oxide (ITO).

Figure 3:
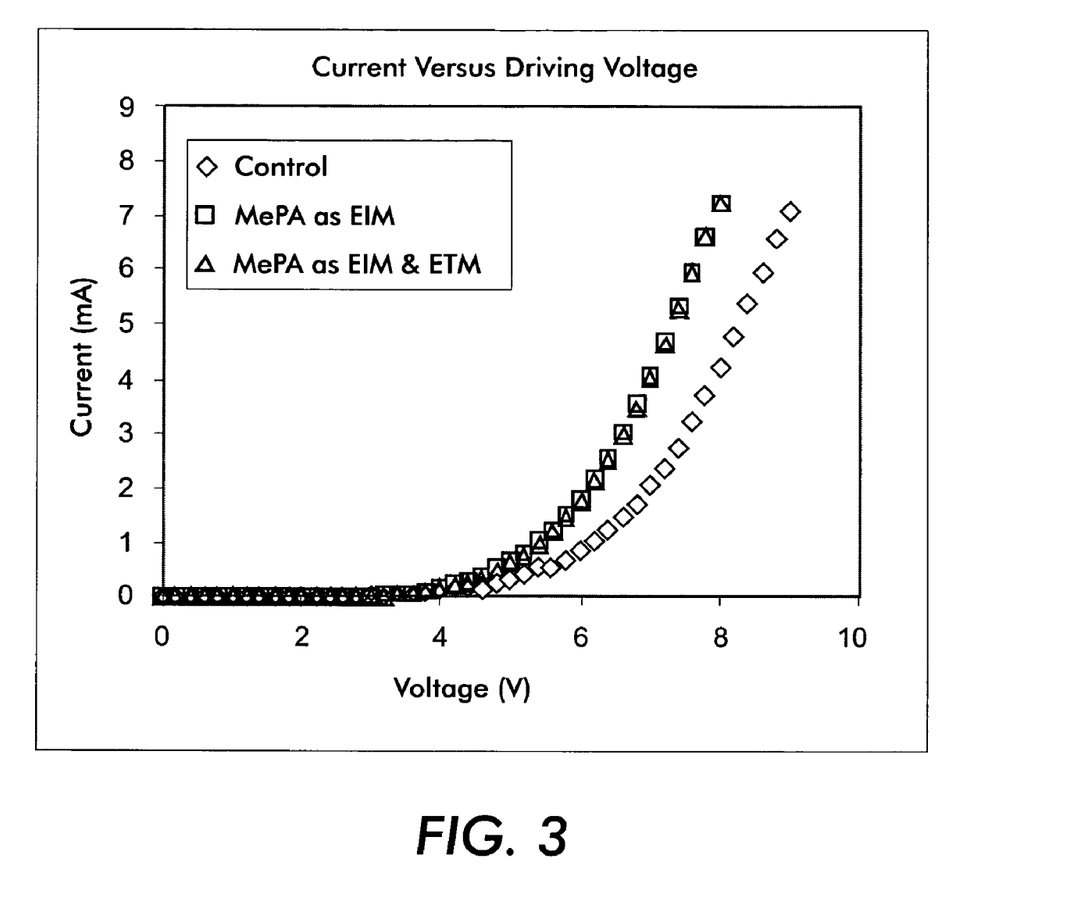
FIG. 3 illustrates the current (mA) versus driving voltage (V) of three OLED configurations, where in all three configurations the OLEDs have the same anodes, cathodes, light emitting region and hole injection and transport layers.
Figure 4:
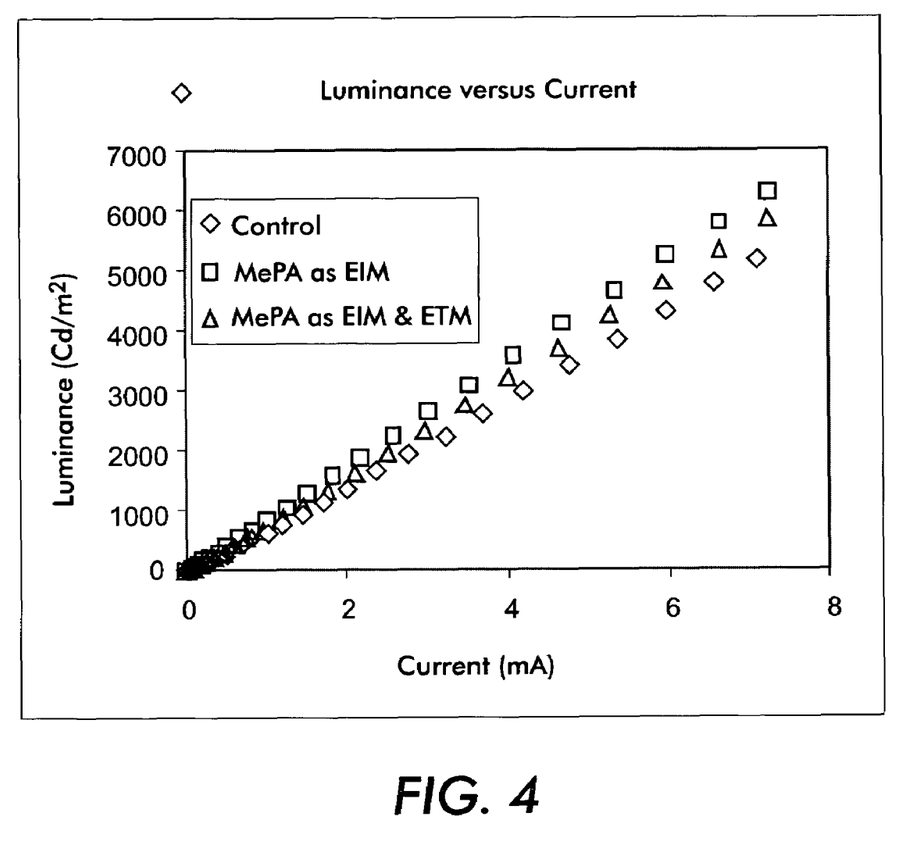
FIG. 4 illustrates the luminance (Gd/mAk$^2$) versus current (mA) of the three OLED configurations.
Figure 5:
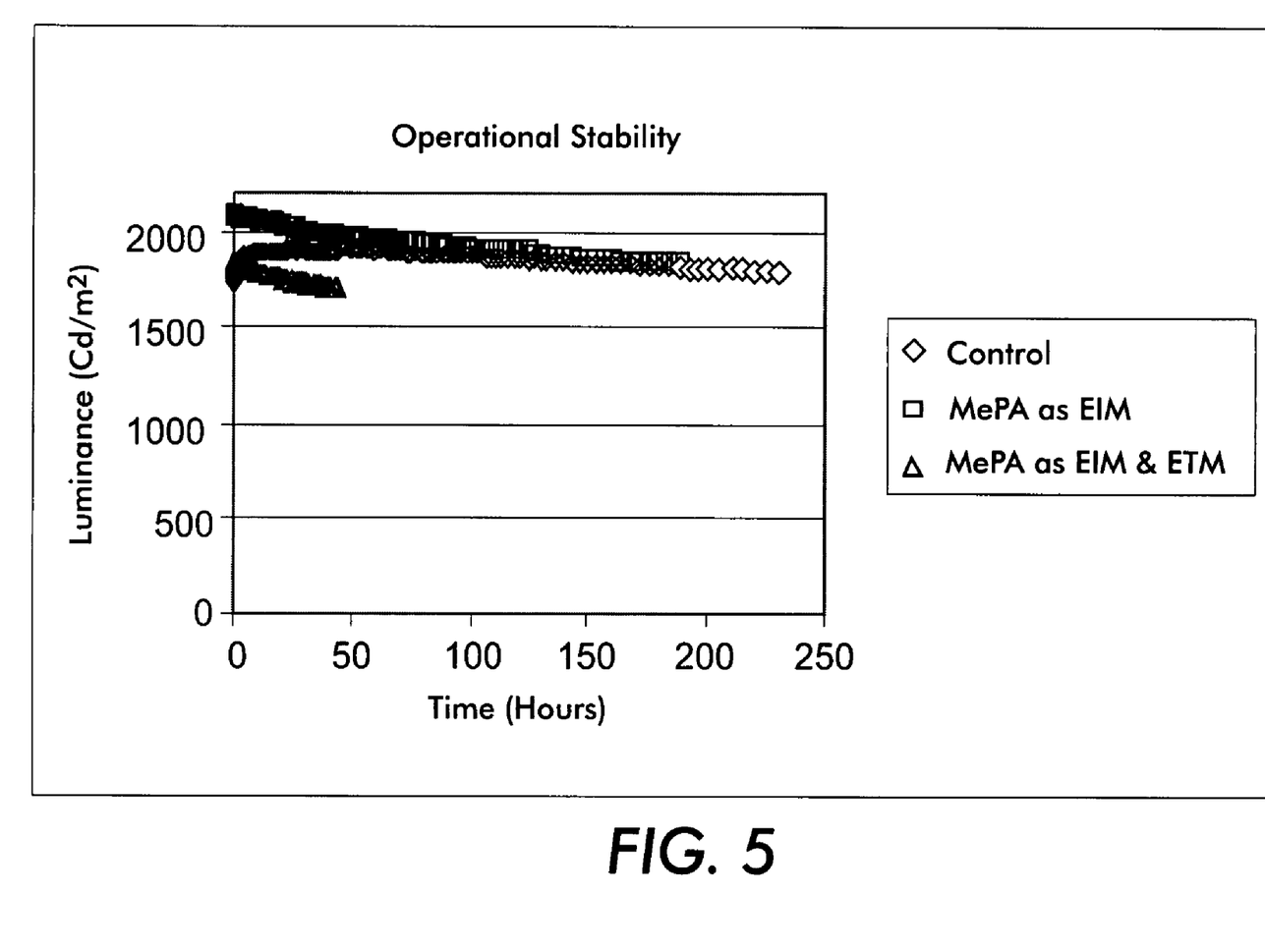
FIG. 5 illustrates the operational stability (luminance (Gd/mA$^2$) versus time (hours) of the three OLED configurations.

FIGS. 3 and 4 show the light-voltage-current characteristics of three OLED configurations described in the following example section and illustrated in FIGS. 2A, 2B and 2C. The control (device C) is shown in FIG. 2A. The MePA device (device A) is shown in FIG. 2B and the MePA device (device B) is shown in FIG. 2C. From these figures it can be seen that the OLEDs containing the MePA in the electron injection and transporting zone demonstrated a substantially lower driving voltage (curves shifted to lower voltages for any given current), while the electroluminescence efficiency (=L/I ratio) somewhat increased. FIG. 5 shows the operational stability versus time of the three OLED configurations. From this figure it is demonstrated that the electroluminescent device comprising an azole compound of the invention improves the operational stability of the device. In the figures, "EIM" refers to electron injection material and "ETM" refers to electron transport material.

The following examples are provided to further illustrate various aspects of this invention, and are not intended to limit the scope of the invention.

EXAMPLE I

Synthesis of Azole Compounds of Formula II

In an illustrative example, an azole compound such as those of Formula (II) can be synthesized as follows:

A 1,10-phenanthroline-5,6-dione was heated at from about 50° C. to about 200° C., more preferably at from 80 to about 150° C., with from about 1 to about 5 equivalents of a suitable aryl aldehyde compound, such as benzaldehyde, 2-naphthaldehyde, 9-anthraldehyde and the like, in the presence of from about 10 to 20 equivalents of ammonium acetate in glacial acetic acid for a suitable time, for instance, about 5 hours. After cooling, the mixture was neutralized with a suitable base such as aqueous ammonia and the precipitate is collected by filtration to give an intermediate compound of 2-(9-aryl)imidazo[4,5-f]-[1,10]phenanthroline. This intermediate compound was then added to, from about 1 to 4 equivalents of a suitable base such as sodium hydride, from about 1 to 5 equivalents of a methylating agents such as iodomethane and suitable amounts of a solvent such as dimethylformamide and is stirred for a suitable time, about 24 hours in which time an alcohol like methanol was added, and the resulting precipitate is collected by filtration and washed with water to give azole compounds of formula II. The crude product may further be purified by standard purification means including recrystallization and sublimation. The azole compound products obtained may be confirmed by elemental analysis, NMR or IR spectrometric identification techniques.

Synthesis of 1-Methyl-2-(9-anthryl)imidazo[4,5-f]-[1,10] phenanthroline

A mixture of 1,10-phenanthroline-5,6-dione (10 grams, purchased from Aldrich Co.), 9-anthraldehyde (14.7 grams) and ammonium acetate (51.4 grams) was placed into a round bottom flask and dissolved in 200 milliliters of glacial acetic acid. The solution was heated under reflux for 4 hours at which time the reaction was cooled to room temperature and diluted with water. The solution was neutralized with concentrated aqueous ammonia and the precipitate was collected by filtration and washed with water and then dichloromethane and dried to give 17 grams of 2-(9-anthryl)imidazo[4,5-f]-[1,10]phenanthroline. The product and its structure was confirmed by proton NMR analysis.

A mixture of the 2-(9-anthryl)imidazo[4,5-f]-[1,10] phenanthroline (10 grams) and sodium hydride (11.5 grams) in 300 milliliters of dimethylformamide was stirred at ambient temperature (about 23° C.) for 30 minutes. Into the resulting mixture was added 18.7 grams of iodomethane. The reaction was stirred overnight at room temperature when 100 milliliters of methanol was added. The precipitate was collected by filtration, washed with water, and dried in a vacuum oven to give the crude product which was further purified by sublimation. The product and its structure was confirmed by proton NMR analysis.

EXAMPLE II

Fabrication of Organic EL Devices of the Invention:

Device A: A 500 Å indium tin oxide (ITO) anode coated glass substrate was selected, the thickness of the glass substrate being about 1 millimeter. The glass was cleaned with a commercial detergent, rinsed with deionized water and dried in a vacuum oven at 60° C. for 1 hour. Immediately before use, the glass was treated with UV ozone for about 0.5 hours.

The ITO anode coated on the glass substrate was then placed in a vacuum deposition chamber and a hole injection and transporting zone was applied. The zone deposition rate and thickness were controlled by an Inficon Model IC/5 controller. Under a pressure of about $5 \times 10^{-6}$ Torr, a 20 nanometers thick buffer was deposited on the ITO glass substrate through the evaporation of N,N'-1-naphthyl-N,N'-diphenyl-1,1'-biphenyl-4,4'-diamine at a rate of 0.6 nanometer/second from a tantalum boat.

Onto the hole injection and transporting zone was deposited a mixed charge transport layer of N,N'-1-naphthyl-N,N'-diphenyl-1,1'-biphenyl-4,4'-diamine at a rate of 0.3 nanometer/second, and tris-(8-hydroxyquinolinato) aluminum at a rate of 0.3 to form a 80 nanometers mixed charge transport layer, by the simultaneous evaporation from two independently controlled tantalum boats containing N,N'-1-naphthyl-N,N'-diphenyl-1,1'-biphenyl-4,4'-diamine and tris-(8-hydroxyquinolinato) aluminum, respectively.

A 20 nanometers thick electron injection and transporting zone was then deposited by evaporation of an azole selected from Examples I to II, such as 2-(9-anthryl)-1-Methylimidazo[4,5-f]-1,10-phenanthroline, at a rate of 0.6 nanometer/second.

A 100 nanometer cathode of a magnesium silver alloy was deposited at a total deposition rate of 0.5 nanometer/second onto the light emitting layer above by the simultaneous evaporation from two independently controlled tantalum boats containing Mg and Ag, respectively. A typical composition was 9:1 in atomic ratio of Mg to Ag. Finally, a 200 nanometer silver layer was overcoated on the Mg:Ag cathode for the primary purpose of protecting the reactive Mg from ambient moisture.

Device B: This device was fabricated in accordance with Device A, except that a 10 nanometer layer of tris-(8-hydroxyquinolinato) aluminum was further deposited on the mixed charge transport layer at a rate of 0.6 nanometers/second. The device was completed by the deposition of 10 nanometer layer of the azole, followed by the deposition of a Mg:Ag cathode.

Device C: This control device was fabricated in accordance with Device A except that tris-(8-hydroxyquinolinato) aluminum was deposited in place of the azole compound of, for example, 2-(9-anthryl)-1-Methylimidazo[4,5-f]-1,10-phenanthroline.

The above EL devices were retained in a dry box, which was continuously purged with nitrogen gas, and the performance thereof was assessed by measuring the current-voltage characteristics and light output under a direct current measurement. The current-voltage characteristics were determined with a Keithley Model 238 High Current Source Measure Unit. The ITO electrode was connected to the positive terminal of the current source. At the same time, the light output from the device was monitored by a silicon photodiode.

The current-voltage and luminance-current characteristics of these devices are shown in FIGS. 3 to 5. The results indicate that the azole compounds of the present invention show superior performance when serving as the electron transport material within the devices.

While the invention has been described in conjunction with the specific embodiments described above, it is evident that many alternatives, modifications and variations are apparent to those skilled in the art. Accordingly, the preferred embodiments of the invention as set forth above are intended to be illustrative and not limiting. Various changes can be made without departing from the spirit and scope of the invention.

The invention claimed is:

1. An electroluminescent device comprising an anode, a cathode, a buffer layer in contact with said anode, and a luminescent region provided between said anode and cathode, said luminescent region comprising;
   an electron injection and transporting zone and at least one of a hole injection and transporting zone and a mixed charge transport layer, wherein said electron injection and transporting zone and/or said mixed charge transporting layer comprises an azole compound of the formula (1):

(I)

wherein one X represents N and the other X represents CH or N;
   Y is an atom or a group selected from the group consisting of O, S, and —N(R)—, wherein R is a hydrocarbyl group of from 1 to about 30 carbons;
   $R^1$ and $R^2$ are each a substituent selected from the group consisting of hydrogen, an alkyl group of from 1 to about 25 carbon atoms, an aryl group of about 6 to about 30 carbon atoms, an alkoxy group of from 1 to about 25 carbon atoms, a halogen, and a cyano group; and
   Ar is an aromatic component.

2. The electroluminescent device of claim 1, wherein said alkyl group has from 1 to about 6 carbon atoms and said alkoxy group has from 1 to about 6 carbon atoms.

3. The electroluminescent device of claim 1, wherein said Ar is an aryl group having from about 6 to about 30 carbons or a heteroaryl group.

4. The electroluminescent device of claim 3, wherein said aryl group is selected from the group consisting of a phenyl, a naphthyl, and an anthryl and said heteroaryl group is selected from the group consisting of a pyridyl and a quinolyl.

5. The electroluminescent device of claim 1, wherein said electron injection and transporting zone is provided adjacent said cathode.

6. The electroluminescent device of claim 5, wherein said electron injection and transporting zone comprises one or more layers.

7. The electroluminescent device of claim 6, wherein at least one of said layers comprises said azole compound of formula I.

8. The electroluminescent device of claim 6, wherein a portion of one or more of said layers comprises said azole compound of formula I.

9. The electroluminescent device of claim 6, wherein a layer in direct contact with said cathode comprises said azole compound of formula I.

10. The electroluminescent device of claim 1, wherein said hole injection and transport zone is provided on said anode, said hole injection and transporting zone comprising compounds selected from the group consisting of aromatic tertiary amines, indolocarbazoles, aromatic hydrocarbons and mixtures thereof.

11. The electroluminescent device of claim 10, wherein a luminescent material is additionally provided in said hole injection and transporting zone and/or said electron injection and transporting zone.

12. The electroluminescent device of claim 1, wherein a mixed charge transport layer is provided in between said electron injection and transporting zone and said anode.

13. The electroluminescent device of claim 12, wherein said mixed charge transport layer comprises an electron transport material and a hole transport material.

14. The electroluminescent device of claim 13, wherein said mixed charge transport layer comprises about 20 wt % to about 80 wt % of the hole transport material.

15. The electroluminescent device of claim 13, wherein electron transport material is selected from the group consisting of an azole compound of formula I, metal chelates, stilbenes, triazines, aromatic hydrocarbons and mixtures thereof.

16. The electroluminescent device of claim 12, wherein said mixed charge transport layer is comprised of a luminescent material.

17. The electroluminescent device of claim 13, wherein said mixed charge transport layer additionally comprises a luminescent material.

18. The electroluminescent device of claim 1, wherein said buffer layer comprises a material selected from the group consisting of a phthalocyanine or derivatives thereof, an aromatic tertiary amine, a polyaniline, a polythiophene and mixtures thereof.

19. An electroluminescent device comprising an anode, a cathode and a luminescent region provided between said anode and cathode, said luminescent region comprising:
   an electron injection and transporting zone and at least one of a hole injection and transporting zone and a mixed charge transport layer, wherein said electron injection and transporting zone and/or said mixed charge transporting layer comprises an azole compound
selected from the group consisting of 1-methyl-2-(phenyl)imidazo [4,5-f]-[1,10] phenanthroline, 1-methyl-2-(2-pyridyl)imidazo[4,5-f]-[1,10] phenanthroline, 1-methyl-2-(1-naphthyl)imidazo[4,5-f]-[1,10] phenanthroline, 1-methyl-2-(9-anthryl)imidazo [4,5-f]-[1,10] phenanthroline, 1-methyl-2-(9-anthryl-10-methyl)imidazo[4,5-f]-[1,10] phenanthroline, 1-methyl-2-(9-anthryl-10-t-butyl)imidazo[4,5-f]-[1,10] phenanthroline, 1-methyl-2-(9-anthryl-10-naphthyl)imidazo[4,5-f]-[1,10] phenanthroline, 1and mixtures thereof.

20. The electroluminescent device of claim 19, wherein said azole compound is 1-methyl-2-(9-anthryl)imidazo[4,5-f]-[1,10] phenanthroline.

21. An electroluminescent device comprising an anode, a cathode and a luminescent region provided between said anode and cathode, said luminescent region comprising:
an electron injection and transporting zone and at least one of a hole injection and transporting zone and a mixed charge transport layer, wherein said electron injection and transporting zone and/or said mixed charge transporting layer comprises an azole compound of the formula (II):

wherein $R^1$, $R^2$, $R^3$, $R^4$ and $R^5$ are each a substituent selected from the group consisting of hydrogen, an alkyl group of from 1 to about 25 carbon atoms, an aryl group of about 6 to about 30 carbon atoms, an alkoxy group with from 1 to about 25 carbon atoms, a halogen, and a cyano group; and
R is a hydrocarbyl group of from 1 to about 30 carbons or an aryl group containing about 6 to about 20 carbons.

22. The electroluminescent device of claim 21, wherein said alkyl for $R^2$, $R^3$, $R^4$ and $R^5$ is selected from the group consisting of methyl, ethyl, propyl and butyl.

23. The electroluminescent device of claim 22, wherein $R^5$ is an aryl group.

24. The electroluminescent device of claim 23, wherein said aryl group for R5 is selected from the group consisting of a phenyl, a naphthyl, an anthryl, and a styryl.

25. The electroluminescent device of claim 21, wherein said electron injection and transporting zone is provided adjacent said cathode.

26. The electroluminescent device of claim 25, wherein said electron injection and transporting zone comprises one or more layers.

27. The electroluminescent device of claim 26, wherein at least one of said layers comprises said azole compound of formula II.

28. The electroluminescent device of claim 25, wherein a portion of one or more of said layers comprises said an azole compound of formula I:

wherein X represents CH or N;
Y is an atom or a group selected from the group consisting of O, S, and —N(R)—, wherein R is a hydrocarbyl group of from 1 about 30 carbons;
$R^1$ and $R^2$ are each a substituent selected from the group consisting of hydrogen, an alkyl group of from 1 to about 25 carbon atoms, an aryl group of about 6 to about 30 carbon atoms, an alkoxy group of from 1 to about 25 carbon atoms, a halogen, and a cyano group; and
Ar is an aromatic component.

29. The electroluminescent device of claim 25, wherein a layer in direct contact with said cathode comprises said an azole compound of formula I:

wherein X represents CH or N;
Y is an atom or a group selected from the group consisting of O, S, and —N(R)—, wherein R is a hydrocarbyl group of from 1 to about 30 carbons;
$R^1$ and $R^2$ are each a substituent selected from the group consisting of hydrogen, an alkyl group of from 1 to about 25 carbon atoms, an aryl group of about 6 to about 30 carbon atoms, an alkoxy group of from 1 to about 25 carbon atoms, a halogen, and a cyano group; and
Ar is an aromatic component.

30. The electroluminescent device of claim 21, wherein said hole injection and transporting zone is provided on said anode, said hole injection and transporting zone comprising compounds selected from the group consisting of aromatic tertiary amines, indolocarbazoles, aromatic hydrocarbons and mixtures thereof.

31. The electroluminescent device of claim 30, wherein said hole injection and transporting zone and/or said electron injection and transporting zone additionally comprises a luminescent material.

32. The electroluminescent device of claim 21, wherein a mixed charge transport layer is provided in between said electron injection and transporting zone and said anode.

33. The electroluminescent device of claim 32, wherein said mixed charge transport layer comprises an electron transport material and a hole transport material.

34. The electroluminescent device of claim 33, wherein said mixed charge transport layer comprises about 20 wt % to about 80 wt % of the hole transport material.

35. The electroluminescent device of claim 34, wherein electron transport material is selected from the group consisting of an azole compound of formula I, metal chelates, stilbenes, triazines, aromatic hydrocarbons and mixtures thereof wherein the azole compound of formula I is:

wherein X represents CH or N;
Y is an atom or a group selected from the group consisting of O, S, and —N(R)—, wherein R is a hydrocarbyl group of from 1 to about 30 carbons;
$R^1$ and $R^2$ are each a substituent selected from the group consisting of hydrogen, an alkyl group of from 1 to about 25 carbon atoms, an aryl group of about 6 to about 30 carbon atoms, an alkoxy group of from 1 to about 25 carbon atoms, a halogen, and a cyano group; and
Ar is an aromatic component.

36. The electroluminescent device of claim 32, wherein said mixed charge transport layer is comprised of a luminescent material.

37. The electroluminescent device of claim 33, wherein said mixed charge transport layer additionally comprises a luminescent material.

38. The electroluminescent device of claim 21, wherein a buffer layer is provided in contact with said anode, said buffer layer comprising a material selected from the group consisting of a phthalocyanine or derivatives thereof, an aromatic tertiary amine, a polyaniline, a polythiophene and mixtures thereof.

39. The electroluminescent device of claim 21, wherein said azole compound is selected from the group consisting of 1-methyl-2-(9-anthryl)imidazo[4,5-f]-[1,10] phenanthroline, 1-methyl-2-(9-anthryl-10-methyl)imidazo[4,5-f]-[1,10] phenanthroline, 1-methyl-2-(9-anthryl-10-t-butyl)imidazo[4,5-f]-[1,10] phenanthroline, 1-methyl-2-(9-anthryl-10-naphthyl)imidazo [4,5-f]-[1,10] phenanthroline and mixtures thereof.

40. The electroluminescent device of claim 39, wherein said azole compound is 1-methyl-2-(9-anthryl)imidazo[4,5-f]-[1,10] phenanthroline.

41. An organic electroluminescent device comprising;
an anode and a cathode; and
a luminescent region provided between said anode and cathode, said luminescent region comprising:
an electron injection and transporting zone adjacent said cathode and a hole injection and transporting zone adjacent said anode, wherein said electron injection and transporting zone comprises one or more azole compounds of a formula I and/or formula II,
wherein a compound of formula I comprises:

wherein one X represents N and the other X represents CH or N;
Y is an atom or a group selected from the group consisting of O, S, and —N(R)—, wherein R is a hydrocarbyl group of from 1 to about 30 carbons:
$R^1$ and $R^2$ are each a substituent selected from the group consisting of hydrogen, an alkyl group of from 1 to about 25 carbon atoms, an aryl group of about 6 to about 30 carbon atoms, an alkoxy group of from 1 to about 25 carbon atoms, a halogen, and a cyano group; and
Ar is an aromatic component; and
a compound of formula II comprises:

wherein $R^1$, $R^2$, $R^3$, $R^4$ and $R^5$ are each a substituent selected from the group consisting of hydrogen, an alkyl group of from 1 to about 25 carbon atoms, an aryl group of about 6 to about 30 carbon atoms, an alkoxy group with from 1 to about 25 carbon atoms, a halogen, and a cyano group; and
R is a hydrocarbyl group of from 1 to about 30 carbons or an aryl group containing about 6 to about 20 carbons.

42. The device of claim 41, wherein said electron injection and transporting zone is provided in direct contact with said cathode.

43. The device of claim 41, wherein said electron injection and transporting zone comprises one or more layers.

44. An organic electroluminescent device comprising;
an anode and a cathode;
a luminescent region provided between said anode and cathode, said luminescent region comprising:
an electron injection and transporting zone adjacent said cathode and a hole injection and transporting zone adjacent said anode, wherein said electron injection and transporting zone comprises one or more layers, and one or more azole compounds of formula I and/or formula II with at least one of said layers comprising an azole compound of formula II, wherein a compound of formula I comprises:

(I)

wherein one X represents N and the other X represents CH or N;

Y is an atom or a group selected from the group consisting of O, S, and —N(R)—, wherein R is a hydrocarbyl group of from 1 to about 30 carbons;

$R^1$ and $R^2$ are each a substituent selected from the group consisting of hydrogen, an alkyl group of from 1 to about 25 carbon atoms, an aryl group of about 6 to about 30 carbon atoms, an alkoxy group of from 1 to about 25 carbon atoms, a halogen, and a cyano group; and Ar is an aromatic component; and a compound of formula II comprises:

(II)

wherein $R^1$, $R^2$, $R^3$, $R^4$ and $R^5$ are each a substituent selected from the group consisting of hydrogen, an alkyl group of from 1 to about 25 carbon atoms, an aryl group of about 6 to about 30 carbon atoms, an alkoxy group with from 1 to about 25 carbon atoms, a halogen, and a cyano group; and R is a hydrocarbyl group of from 1 to about 30 carbons or an aryl group containing about 6 to about 20 carbons.

45. The device of claim 43, wherein a portion of one or more of said layers comprises said azole compound of formula I.

46. The device of claim 45, wherein a layer in direct contact with said cathode comprises said azole compound of formula I.

47. The device of claim 41, wherein said hole injection and transporting zone is provided in direct contact with said anode, said hole injection and transporting zone comprising compounds selected from the group consisting of aromatic tertiary amines, indolocarbazoles, aromatic hydrocarbons and mixtures thereof.

48. The device of claim 41, wherein said hole injection and transporting zone and/or said electron injection and transporting zone additionally comprises a luminescent material.

49. The device of claim 41, wherein a mixed charge transport layer is provided in between said electron injection and transporting zone and said anode.

50. The device of claim 49, wherein said mixed charge transport layer comprises an electron transport material and a hole transport material.

51. The device of claim 50, wherein said mixed charge transport layer comprises about 20 wt % to about 80 wt % of the hole transport material.

52. The device of claim 51, wherein electron transport material is selected from the group consisting of an azole compound of formula I, metal chelates, stilbenes, triazines, aromatic hydrocarbons and mixtures thereof.

53. The device of claim 49, wherein said mixed charge transport layer is comprised of a luminescent material.

54. The device of claim 50, wherein said mixed charge transport layer additionally comprises a luminescent material.

55. The device of claim 41, wherein said buffer layer comprises a material selected from the group consisting of a phthalocyanine or derivatives thereof, an aromatic tertiary amine, a polyaniline, a polythiophene and mixtures thereof.

56. An organic electroluminescent device comprising:
an anode and a cathode;
a luminescent region provided between said anode and cathode, said luminescent region comprising:
an electron injection and transporting zone adjacent said cathode and a hole injection and transporting zone adjacent said anode, wherein said electron injection and transporting zone comprises one or more azole compounds
is selected from the group consisting of 1-methyl-2-phenyl)imidazo [4,5-f]-[1,10] phenanthroline, 1-methyl-2-(2-pyridyl)imidazo[4,5-f]-[1,10] phenanthroline, 1-methyl-2-(1-naphthyl)imidazo[4,5-f]-[1,10] phenanthroline, 1-methyl-2-(9-anthryl)imidazo[4,5-f]-[1,10] phenanthroline, 1-methyl-2-(9-anthryl-10-methyl) imidazo [4,5-f]-[1,10] phenanthroline, 1-methyl-2-(9-anthryl-10-t-butyl)imidazo[4,5-f]-1,10] phenanthroline, 1-methyl-2-(9-anthryl-10-naphthyl)imidazo [4,5-f]-[1,10] phenanthroline and mixtures thereof.

57. The device of claim 56, wherein said azole compound is 1-methyl-2-(9-anthryl)imidazo[4,5-f]-[1,10] phenanthroline.

58. A method to reduce power consumption and increase power conversion efficiency in an organic light emitting device comprising an anode, a cathode, a buffer layer in contact with said anode, and a luminescent region provided between said anode and cathode, said luminescent region comprising:
an electron injection and transporting zone and at least one of a hole injection and transporting zone and a mixed charge transport layer,
wherein said method comprises providing an azole compound of a formula I and/or formula II in said electron injection and transporting zone and/or said mixed charge transporting layer, wherein a compound of formula I comprises:

(I)

wherein one X represents N and the other X represents CH or N;

Y is an atom or a group selected from the group consisting of O, S, and —N(R)—, wherein R is a hydrocarbyl group of from 1 to about 30 carbons;

$R^1$ and $R^2$ are each a substituent selected from the group consisting of hydrogen, an alkyl group of from 1 to about 25 carbon atoms, an aryl group of about 6 to about 30 carbon atoms, an alkoxy group of from 1 to about 25 carbon atoms, a halogen, and a cyano group; and Ar is an aromatic component; and a compound of formula II comprises:

(II)

wherein $R^1$, $R^2$, $R^3$, $R^4$ and $R^5$ are each a substituent selected from the group consisting of hydrogen, an alkyl group of from 1 to about 25 carbons atoms, an aryl group of about 6 to about 30 carbon atoms, an alkoxy group with from 1 to about 25 carbon atoms, a halogen, and a cyano group; and R is a hydrocarbyl group of from 1 to about 30 carbons or an aryl group containing about 6 to about 20 carbons.

59. An electron transport material comprising an azole compound of the following formula:

(II)

wherein $R^1$, $R^2$, $R^3$, $R^4$ and $R^5$ are each a substituent selected from the group consisting of hydrogen, an alkyl group of from 1 to about 25 carbon atoms, an aryl group of about 6 to about 30 carbon atoms, an alkoxy group with from 1 to about 25 carbon atoms, a halogen, and a cyano group; and R is a hydrocarbyl group of from 1 to about 30 carbons or an aryl group containing about 6 to about 20 carbons.

60. A photoreceptor, solar cell and/or organic electronic device comprising the electron transport material of claim 59.

61. An electroluminescent device comprising an anode, a cathode, a buffer layer in contact with said anode, and a luminescent region provided between said anode and cathode, said luminescent region comprising;

an electron injection and transporting zone and at least one of a hole injection and transporting zone and a mixed charge transport layer, wherein said electron injection and transporting zone and/or said mixed charge transporting layer comprises an azole compound of formula (I):

(I)

wherein X represents CH or N;

Y is an atom or a group selected from the group consisting of O, S, and —N(R)—, wherein R is a hydrocarbyl group of from 8 to about 30 carbons;

$R^1$ and $R^2$ are each a substituent selected from the group consisting of hydrogen, an alkyl group of from 1 to about 25 carbon atoms, an aryl group of about 6 to about 30 carbon atoms, an alkoxy group of from 1 to about 25 carbon atoms, a halogen, and a cyano group; and Ar is an aromatic component.

62. The organic electroluminescent device of claim 41, further comprising a buffer layer in contact with the anode.

* * * * *